United States Patent [19]

Lubowitz et al.

[11] Patent Number: 4,661,604

[45] Date of Patent: Apr. 28, 1987

[54] MONOFUNCTIONAL CROSSLINKING IMIDOPHENOLS

[75] Inventors: Hyman R. Lubowitz, Rolling Hills Estates, Calif.; Clyde H. Sheppard, Bellevue, Wash.

[73] Assignees: TRW, Inc., Redondo Beach, Calif.; The Boeing Company, Seattle, Wash.

[21] Appl. No.: 522,676

[22] Filed: Aug. 12, 1983

Related U.S. Application Data

[62] Division of Ser. No. 274,162, Jun. 16, 1981.

[51] Int. Cl.[4] .......................................... C07D 209/56
[52] U.S. Cl. ................................... 548/435; 528/173; 548/547
[58] Field of Search .................. 524/89; 548/435, 476, 548/547; 528/173, 170; 526/259, 262

[56] References Cited

U.S. PATENT DOCUMENTS

| | | |
|---|---|---|
| Re. 29,316 | 7/1977 | Bargain et al. |
| 3,236,808 | 2/1966 | Goldberg et al. |
| 3,262,914 | 7/1966 | Goldberg et al. |
| 3,265,708 | 8/1966 | Stiteler .............................. 260/326.5 |
| 3,355,272 | 11/1967 | D'Alessandro . |
| 3,453,236 | 7/1969 | Culbertson . |
| 3,454,673 | 7/1969 | Schmidt et al. |
| 3,530,087 | 9/1970 | Hays et al. |
| 3,536,670 | 10/1970 | Aclony et al. |
| 3,549,231 | 12/1970 | Scidmore et al. |
| 3,562,232 | 2/1971 | Bargain et al. |
| 3,563,951 | 2/1971 | Radlmann et al. |
| 3,631,222 | 12/1971 | Vogel et al. |
| 3,641,207 | 2/1972 | Lauchlan et al. |
| 3,652,710 | 3/1972 | Holub et al. |
| 3,658,938 | 4/1972 | Kwiatkowski et al. |
| 3,663,507 | 5/1972 | Vogel et al. |
| 3,699,075 | 10/1972 | Lubowitz et al. |
| 3,708,439 | 1/1973 | Sayigh et al. |
| 3,729,446 | 4/1973 | Holub et al. |
| 3,749,735 | 7/1973 | Lorin et al. .......................... 548/435 |
| 3,761,441 | 9/1973 | D'Alessandro et al. ......... 260/37 N |
| 3,763,101 | 10/1973 | Jones et al. |
| 3,770,697 | 11/1973 | Holub et al. |
| 3,773,718 | 11/1973 | Klebe et al. |

(List continued on next page.)

FOREIGN PATENT DOCUMENTS

45-9393 4/1970 Japan .
9120993 11/1974 Japan .
2002378 4/1983 United Kingdom .

OTHER PUBLICATIONS

"Kinetics and Mechanism of Diers-Alder Condensation of Hexachlorocyclopentadiene . . . " *Organic React,* Salakhov et al., 1979, 65-74.
"Kinetics and Mechanism . . . with Cyclic Dienophiles", *Org. React,* (Tartu), Salakhov et al., pp. 75-83.
Sheppard, C. H., House, E. E. and Stander, E. "Advanced Thermoplastic Composite Development" 36th Annual Conference, Reinforced Plastics Composites Institute, The Society of the Plastic Industry Inc., Feb. 16-20, 1981.
Sheppard, C. H. and House, E. E. "Development of Modified Polysulfone Resins" Final Report and Contract N 00019-80-C-0609, Boeing Aerospace Company, Seattle, Washington 98124, Dec. 1981.

*Primary Examiner*—Deborah L. Kyle
*Assistant Examiner*—T. J. Wallen
*Attorney, Agent, or Firm*—Finnegan, Henderson, Farabow, Garrett & Dunner

[57] ABSTRACT

Resins are prepared from polysulfone and polyethersulfone polymers that bear functional groups derived from compounds that are condensation products of aminophenols and acid anhydrides. The polymers are prepared by coreacting aromatic compounds holding two hydroxyl groups, aromatic compounds holding two active halogen groups, and the condensation product of amino-phenol and acid anhydride, the condensation product holding one hydroxyl group. The resulting product has a molecular weight between about 1,000 and 40,000, preferably between about 5,000 and 30,000, and can be cross-linked to form a resin that is thermoplastic and solvent resistant.

4 Claims, 1 Drawing Figure

U.S. PATENT DOCUMENTS

| | | | |
|---|---|---|---|
| 3,787,363 | 11/1974 | Staniland et al. | |
| 3,803,081 | 4/1974 | Lubowitz et al. | |
| 3,812,159 | 5/1974 | Lubowitz | |
| 3,839,287 | 10/1974 | Kwiatkowski et al. | 260/49 |
| 3,859,252 | 1/1975 | Cho | |
| 3,879,349 | 4/1975 | Bilow et al. | |
| 3,896,147 | 7/1975 | Stephen | 524/89 |
| 3,897,393 | 7/1975 | Lee | |
| 3,897,395 | 7/1975 | D'Alelio | |
| 3,920,768 | 11/1975 | Kwiatkowski | |
| 3,935,167 | 1/1976 | Marvel et al. | |
| 3,941,746 | 3/1976 | Stephen | 524/89 |
| 3,956,320 | 5/1976 | Heath et al. | |
| 3,957,862 | 5/1976 | Heath et al. | |
| 3,970,714 | 7/1976 | Bargain | |
| 3,972,902 | 8/1976 | Heath et al. | |
| 3,975,862 | 8/1976 | Doan | |
| 3,988,374 | 10/1976 | Brode et al. | |
| 3,993,630 | 11/1976 | Darmory et al. | |
| 3,998,786 | 12/1976 | D'Alelio et al. | |
| 4,000,146 | 12/1976 | Gerber | |
| 4,005,134 | 1/1977 | Markezich | |
| 4,020,069 | 4/1977 | Johnson et al. | |
| 4,026,871 | 5/1977 | D'Alelio | |
| 4,058,505 | 11/1977 | D'Alelio | |
| 4,060,515 | 11/1977 | D'Alelio | |
| 4,064,289 | 12/1977 | Yokoyama et al. | |
| 4,097,456 | 6/1978 | Barie | |
| 4,100,137 | 7/1978 | Lemieux et al. | |
| 4,100,138 | 7/1978 | Bilow et al. | |
| 4,101,488 | 7/1978 | Ishizuka | |
| 4,107,153 | 8/1978 | Akiyama et al. | |
| 4,108,837 | 8/1978 | Johnson et al. | |
| 4,108,926 | 8/1978 | Arnold et al. | |
| 4,115,231 | 9/1978 | Darms | |
| 4,116,937 | 9/1978 | Jones et al. | |
| 4,126,619 | 11/1978 | Darms et al. | |
| 4,128,574 | 12/1978 | Markezich et al. | |
| 4,166,168 | 8/1979 | D'Alelio | |
| 4,168,366 | 9/1979 | D'Alelio | |
| 4,175,175 | 11/1979 | Johnson | |
| 4,176,223 | 11/1979 | Irwin | |
| 4,179,551 | 11/1979 | Jones et al. | |
| 4,183,839 | 1/1980 | Gagliana | |
| 4,189,560 | 2/1980 | Roth et al. | |
| 4,197,397 | 4/1980 | D'Alelio | |
| 4,206,106 | 6/1980 | Heilman et al. | |
| 4,218,555 | 8/1980 | Antonoplos et al. | |
| 4,239,883 | 12/1980 | Stenzenberger | |
| 4,251,417 | 2/1981 | Chow et al. | |
| 4,251,418 | 2/1981 | Chow et al. | |
| 4,251,419 | 2/1981 | Heilman et al. | |
| 4,251,420 | 2/1981 | Antonoplos | |
| 4,255,313 | 3/1981 | Antonoplos et al. | |
| 4,269,961 | 5/1981 | Jones | |
| 4,273,916 | 6/1981 | Jones | |
| 4,276,407 | 6/1981 | Bilow et al. | |
| 4,288,607 | 9/1981 | Bier et al. | |
| 4,293,670 | 10/1981 | Robeson et al. | |
| 4,297,472 | 10/1981 | Heiss | |
| 4,297,474 | 10/1981 | Williams, III et al. | |
| 4,298,720 | 11/1981 | Yamazaki et al. | |
| 4,299,750 | 11/1981 | Antonoplos et al. | |
| 4,375,427 | 3/1983 | Miller et al. | |
| 4,386,848 | 6/1983 | Cleudenin et al. | |
| 4,398,821 | 8/1983 | Stewart | |
| 4,405,770 | 9/1983 | Schoenberg et al. | |

MONOFUNCTIONAL CROSSLINKING IMIDOPHENOLS

The Government has rights in this invention pursuant to Contract No. N00019-79-C-0203 awarded by the United States Navy.

This is a division of application Ser. No. 06/274,162, filed June 16, 1981.

BACKGROUND OF THE INVENTION

The present invention relates to resins containing polymer chains that bear functional chemical groups and to the products thereof. In particular, linear polysulfone and polyethersulfone polymers or oligomers are synthesized with thermally and/or chemically active groups at the ends of the chains. These groups, at a subsequent time, are activated to yield chemically crosslinked polysulfones and polyethersulfones.

For many applications, it is desirable to employ thermoplastic resins. Although such resins and their application areas are well known, the use of thermoplastic resin reinforced by fiber is a relatively new art. The advantages of this art, however, are significant. Fiber toughens and stiffens the resin to produce high-performance products. At the same time, processing is facilitated because the fiber-reinforced resin maintains its thermoplastic character. For example, a sheet of fiber-reinforced resin can be heated and then stamped into desired shapes with appropriate metal dies. Furthermore, shapes can be altered when desired.

On the other hand, although thermosetting resins are generally used in fabricating fiber-reinforced composites, fashioning shapes by thermoforming is not readily possible when thermosetting resins are used. Such products must be fashioned within the constraints of dies. Once formed, they cannot be reshaped; thus, errors are not correctable and shape adjustments are not possible. A sheet of fiber-reinforced thermosetting resin, fully cured, cannot be thermoformed into desired shapes.

Although thermoplastic resins exhibit processing advantages over thermosetting resins, they exhibit, in general, a serious deficiency in properties, i.e., the tendency to be solvated and thus weakened by organic solvents. This deficiency has severely limited application of fiber-reinforced thermoplastic resin composites. For example, in the preparation of circuit boards, boards prepared from fiber-reinforced thermoplastic resin composites cannot be cleaned by solvents commonly used in the manufacture of circuit boards. In the use of thermoplastic components for aircraft, a significant amount of product loss is incurred when aircraft hydraulic fluids and cleaning fluids come into contact with the composites.

SUMMARY OF THE INVENTION

One of the objects of the present invention is to provide a series of thermoplastic resins that resist attack by organic solvents.

Another object is to provide thermoplastic resins composed by polymers having aromatic-group-containing backbones. Such backbones contribute to the thermal stability of the resins.

It is another object of the invention to provide solvent-resistant polysulfone and polyethersulfone polymers that can be crosslinked by thermal and/or chemical activation.

It is another object of this invention to realize thermally stable resins that resist chemical stress corrosion, particularly in the presence of organic solvents.

Another object of the present invention is to provide compositions that are suitable for use as laminating materials and as adhesives.

Another object is to provide laminates that can be thermoformed.

Another object is to provide laminates that are tough, thermally stable, and resistant to attack by solvents.

Another object is to provide laminates that are chemically stable, particularly against oxidation.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the polysulfone or polyethersulfone polymer of the invention is a product of:

(1) 2 moles per (2) $n+1$ moles Z—R—Z and
(3) n moles OH—R'—OH,
wherein X is selected from the group consisting of

R" is hydrogen or a lower alkyl, Z is selected from the group consisting of fluorine, chlorine, and bromine, and preferably is chlorine, R is an aromatic radical, R' is an aromatic radical, and n is selected so that the polymer has a molecular weight between about 1,000 and about 40,000. The preferred molecular weight for this precursor polymer is between about 5,000 and about 30,000, more preferably between about 10,000 and 20,000. Preferably R is selected from the group consisting of and

-continued

R' is selected from the group consisting of

, and

E, $E_1$, $E_2$, and $E_3$ each represent substituent groups selected from the group consisting of halogen, alkyl groups having 1 to 4 carbon atoms and alkoxy groups having 1 to 4 carbon atoms, and a and b are each an integer having a value of 0 to 4.

Further to achieve the foregoing objects and in accordance with the purpose of the invention, as embodied and broadly described herein, the compound of the invention has the formula:

wherein X is selected from the group consisting of and R'' is hydrogen or lower alkyl.

Still further to achieve the foregoing objects and in accordance with the purpose of the invention, as embodied and broadly described herein, the method of the invention for synthesizing the aforementioned compound comprises reacting a compound having the formula with a compound having the formula in a solvent in the presence of an inert atmosphere.

Still further to achieve the foregoing objects and in accordance with the purpose of the invention, as embodied and broadly described herein, the method for making the aforementioned polymer comprises (a) mixing compounds (1), (2), and (3) and a scavenger in a solvent in the presence of an inert atmosphere, and (b) heating the mixture to react the compounds.

Figure 1:
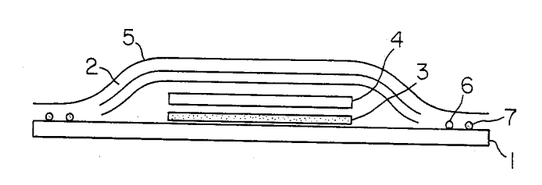
The drawing illustrates the curing of fabric impregnated with the polymer of the present invention in a vacuum bag.

The accompanying drawing, which is incorporated in and constitutes a part of this specification, illustrates a method of curing the polymer of the present invention and, together with the description, serves to explain the principles of the invention.

DESCRIPTION OF THE PREFERRED EMBODIMENTS

Reference will now be made in detail to the presently preferred embodiments of the invention.

The objects of this invention are realized through the use of resins prepared from polysulfone and polyethersulfone polymers that bear functional groups. The functional groups are derived from compounds that are condensation products of amino-phenols and acid anhydrides. The polymers are prepared in solvent polymerization by coreacting aromatic compounds holding two hydroxyl groups, aromatic compounds holding two active halogen groups, preferably chlorine groups, and the condensation product of amino-phenol and acid anhydride, the condensation product holding one hydroxyl group. The polymer product molecular weights are adjusted by predetermined combinations of the three components: dihydroxy compounds, dihalo compounds, and monohydroxy compounds.

In accordance with the invention, as embodied herein, the cross-linkable polysulfone or polyethersulfone polymer of the present invention is formed by reacting:

(1) 2 moles per (2) n+1 moles Z—R—Z and
(3) n moles OH—R'—OH,
wherein X is selected from the group consisting of R" is hydrogen or a lower alkyl, Z is selected from the group consisting of fluorine, chlorine, and bromine, and preferably is chlorine, R is an aromatic radical, R' is an aromatic radical, and n is selected so that the polymer has a molecular weight between about 1,000 and about 40,000. The resulting product has the formula:

This reaction is carried out by mixing the three compounds with a scavenger in a solvent in the presence of an inert atmosphere and heating the mixture to react the compounds. Preferred scavengers are potassium carbonate and sodium carbonate. Other scavengers such as sodium hydroxide and potassium hydroxide may also be useful. The scavenger is preferably used in slight excess of molar quantities, e.g., about 10% more than molar quantities, and ensures that the solution remains basic. It is also possible that the scavenger participates in the reaction. In any event, the scavenger should be employed in the reaction to form the oligomeric composition.

The OH group of the compound holding one hydroxyl group is reactive, as are the OH groups of the aromatic compounds holding two hydroxyl groups, which makes the reaction possible. As indicated above, the molecular weight of the resulting oligomer should be between about 1,000 and about 40,000, but it is preferably between about 5,000 and 30,000, and still more preferably between about 10,000 and 20,000. Mixtures of oligomers having molecular weights within these ranges may also be used, for example a mixture of an oligomer having a molecular weight of 10,000 with one having a molecular weight of 20,000, or a mixture of an oligomer with a molecular weight of 5,000 with one having a molecular weight of 10,000 or 20,000. Within these ranges, the oligomers can be cross-linked to form polymers that are insoluble while retaining thermoplasticity. The oligomer itself, however, is soluble and therefore may be easily processed, such as by impregnating a fabric of glass or other appropriate material.

An oligomer with a molecular weight lower than about 1,000 would undergo excessive cross-linking and lose its thermoplastic properties and, consequently, suffer the disadvantages of thermosetting resins. If the oligomer has a molecular weight more than about 40,000, insufficient cross-linking will occur, and the resulting resin will have inadequate solvent resistance, as with prior thermoplastic resins. Within the ranges described above, however, the cross-linked oligomer has the beneficial properties of both thermoplastic and thermosetting resins without the disadvantages of either.

Typical compounds holding two hydroxyl groups that may be used in the process of the invention include:

TABLE I hydroquinone bisphenol A para, para' bisphenol

4,4' dihydroxyldiphenylsulfide 4,4' dihydroxydiphenylsulfone 4,4' dihydroxydiphenylether 4,4' dihydroxydiphenylhexafluoropropane Each of the illustrated compounds holding two hydroxyl groups could also be replaced by the ortho or meta isomer. Moreover, mixtures of the compounds holding two hydroxyl groups may be used. The compounds may be substituted on the aromatic rings with halogens or alkyl groups having 1 to 4 carbon atoms and alkoxy groups having 1 to 4 carbon atoms. The preferred compound is bisphenol A, but replacing a portion of the bisphenol A with other selected compounds holding two hydroxyl groups can add rigidity to the product without increasing the molecular weight, and therefore can render the cross-linked oligomer more solvent resistant. The different compounds holding two hydroxyl groups may be added in such a manner that the oligomer is a random or a block copolymer.

Typical compounds holding two active halogens that may be used in the process of this invention include:

TABLE II

[Structure: 4,4' dichlorodiphenylsulfone]

4,4' dichlorodiphenylsulfone

[Structure: 4,4' dichlorodiphenylthioether]

4,4' dichlorodiphenylthioether

[Structure: 4,4' dichlorodiphenylhexafluoropropane]

4,4' dichlorodiphenylhexafluoropropane

Again, the two active chlorines could each be in the ortho or meta position as well. Furthermore, the chlorine atoms could be replaced by fluorine or bromine. As indicated above, both the compounds holding two hydroxyl groups and the compounds holding two active halogens may be substituted on the aromatic rings with halogens or alkyl groups having 1 to 4 carbon atoms and alkoxy groups having 1 to 4 carbon atoms.

Typical compounds holding one hydroxyl group that may be used in the process of this invention include:

TABLE III

[Structures with R'', N, OH groups]

TABLE III-continued

[Structures with R'', N, OH groups]

where R'' equals hydrogen atom or a lower alkyl group. By lower alkyl group is meant an alkyl group having 1 to 8 carbon atoms.

The polysulfone and polyethersulfone polymers prepared from combinations of compounds from Tables I, II, and III are capable of cross-linking upon the application of heat. Heating temperatures suitable for "curing" the polymers are in the range of 450° to 700° F., with the preferred range being 500° to 650° F.

The polysulfone and polyethersulfone polymers prepared from combinations of compounds from Tables I, II, and III are also capable of cross-linking upon coreaction with suitable coreactants and application of heat. Heating temperatures suitable for "curing" the polymers in the presence of coreactants are in the range of 150° to 700° F., with the preferred range being 450° to 650° F. Roughly equivalent quantities of coreactant and oligomer may be used, with an excess of coreactant being preferred to insure that most reactive sites are used.

Coreactants suitable for cross-linking polysulfone and polyethersulfone polymers containing the maleic group are given in Table IV.

TABLE IV paraphenylenediamine

TABLE IV-continued benzidine 4,4' methylenedianiline where R is an alkyl having 2 to 6 carbon atoms.

Coreactants suitable for cross-linking polysulfone and polyethersulfone polymers containing the norbornene group are given in Table V.

TABLE V where R is an alkyl having 2 to 6 carbon atoms or an aromatic radical such as:

and R" is hydrogen or a lower alkyl.

Coreactants suitable for cross-linking polysulfone and polyethersulfone polymers containing the acetylene group are given in Table VI.

TABLE VI where R is the same as in Table V.

The coreactants accelerate the curing reaction and increase the solvent resistance while decreasing the thermoplasticity of the resin.

The compound holding one hydroxyl group in accordance with the present invention may be synthesized by reacting a compound having the formula with a compound having the formula in a solvent in the presence of an inert atmosphere.

The polymer of the invention, as embodied herein, may be used to form a prepreg by impregnating a fabric with the polymer. The prepreg may then be cured, such as by vacuum bagging and heating at an elevated temperature while under pressure. This is illustrated in the drawing, in which 1 is a caul (a metal backing for applying a surface finish), 2 is a vacuum source, 3 is the prepreg, 4 is a pressure plate, 5 is a Kapton film (duPont polyamide film), 6 is a silicon sealant, and 7 is Kisch (zinc chromate tape).

The following examples are presented to illustrate the various features of the invention.

EXAMPLES OF SYNTHESIS OF COMPOUNDS FROM TABLE III

Example 1

4-hydroxyphenylnadimide

Under dry $N_2$, a solution of 54.56 grams para aminophenol (0.5 mole) and 164.16 grams 5-norbornene 2,3-dicarboxylic anhydride (1 mole) at 20 percent solids in a 67/33 mixture by weight of toluene/n,n-dimethylacetamide continue to reflux until no more water is observed to collect in a Dean Stark trap. Cool to ambient conditions. Slowly pour solution into cold water (approximately 4 water to 1 solution by volume) in a Waring blender. Filter precipitate and wash well with water. Dry the precipitate overnight at 80° C. in an air-circulating oven (mp. 249°–252° C.). Yields near 100 percent should be achieved. The product can be recrystallized from acetone to get a sharp melting point at 250° C.

Example 1'

Example 1 is repeated, except that 109.13 grams para aminophenol (1.0 mole) and 196.99 grams 5-norbornene 2,3-dicarboxylic anhydride (1.2 mole) are used. Yields near 100% should be achieved.

Example 1"

Example 1 is repeated, except that 109.13 grams para amino-phenol (1.0 mole) are used. Yields near 100% should be achieved. Example 2

3-hydroxyphenylnadimide

The procedure used is the same as in Example 1, except use (0.5 mole) meta-aminophenol and (0.5 mole) 5-norbornene 2,3-dicarboxylic anhydride at 50 percent solids in a 67/33 mixture by weight of n,n-dimethylformamide/toluene. An 87 percent yield, mp. 198°–205° C., is achieved.

Recrystallization from methanol by the addition of water gives a melting point of 199°–204° C.

Example 3

4-hydroxyphenylmaleimide

To a solution under dry $N_2$ of 54.56 grams para aminophenol (0.5 mole) at 25 percent solids in DMF, add a solution of 49.03 grams maleic anhydride (0.5 mole) at 50 percent solids in DMF at a rate sufficient to keep the temperature below 70° C. Stir solution 15 minutes. Add 122.51 grams acetic anhydride (1 mole+20% molar excess) and 9.84 grams sodium acetate (0.1 mole+20% molar excess). Heating the resulting mixture to 50° C. and maintain for 1.5 hours. At this point, the whole mass yields a yellow precipitate. Filter the cool precipitate, wash well with water, dry in vacuum oven at 40° C. overnight. The product achieved has a melting point of 158°–162° C.

OLIGOMERIC COMPOSITIONS

Example 4

Formula molecular weight (FMW) 20,000, Para Nadic Cap

In a 1000 ml resin kettle fitted with a mechanical stirrer, thermometer, condenser, Dean Stark trap, and under dry $N_2$, add 511.2 grams of dimethylacetamide and 255.6 grams of toluene. Charge 4.39 grams (0.017 mole) compound obtained in Example 1, 110.07 grams (0.383 mole) dichlorodiphenylsulfone, 85.53 grams (0.375 mole) bisphenol A, and 55.6 grams potassium carbonate. Heat the mixture to 140° C. and hold for 96 hours. Raise temperature of mixture of 160°–165° C. by removing toluene into Dean Stark trap and then hold mixture for 1 hour. Cool mixture to ambient conditions.

Slowly pour solution into cold water (approximately 4 water to 1 solution by volume) in a Waring blender. Filter precipitate and wash until no inorganic chloride is in wash solution. (This is determined by testing wash water with a 25% solution of silver nitrate. A white precipitate of silver chloride is obtained if inorganic chloride is present.) Dry precipitate in air-circulating oven at 68° C.

Example 5

FMW 10,000, Meta Nadic Cap

Use the same procedure as in Example 4, except charge the following quantities of ingredients: 4.74 grams compound from Example 2, 108.0 grams dichlorodiphenylsulfone, 83.93 grams bis-phenol A, 62.37 grams potassium carbonate.

Example 6

FMW 20,000, Para Nadic Cap 10% Excess, 20% Excess $K_2CO_3$

In a 3000-ml resin kettle fitted with a mechanical stirrer, thermometer, condenser, Dean Stark trap, and under dry $N_2$, add 1723.8 grams of dimethylacetamide and 517.14 grams of toluene. Charge 4.74 grams (0.018 mole) compound obtained in Example 1, 107.95 grams (0.376 mole) dichlorodiphenylsulfone, 83.89 grams (0.367 mole) bisphenol A, and 62.36 grams (0.446 mole) potassium carbonate. Heat the mixture to 140° C. and hold for 72 hours. Raise temperature of mixture to 160°–165° C. by removing toluene into Dean Stark trap and then hold mixture for 1 hour. Cool mixture to ambient conditions.

Slowly pour solution into cold water (approximately 4 water to 1 solution by volume) in a Waring blender. Filter precipitate and wash until no inorganic chloride is in wash solution. Dry precipitate in air-circulating oven at 68° C.

Example 7

FMW 10,000, Maleic Cap

Use the same procedure as for Example 4, except charge the following quantities of ingredients: 3.26 grams compound obtained from Example 3, 54.99 grams dichlorodiphenylsulfone, 41.75 grams bisphenol A, 27.79 grams potassium carbonate.

Example 8

FMW 20,000, Maleic Cap

Use the same procedure as for Example 4, except charge the following quantities of ingredients: 3.60 grams compound obtained from Example 3, 111.4 grams dichlorodiphenylsulfone, 86.57 grams bisphenol A, 64.32 grams potassium carbonate.

Example 9

FMW 5,000, Para Nadic Cap

Use the same procedure as for Example 4, except charge the following quantities of ingredients: 8.84 grams compound obtained from Example 1, 52.99 grams dichlorodiphenylsulfone, 38.17 grams bisphenol A, 26.78 grams potassium carbonate.

Example 10

(General method of preparation of composites for oligomers of Examples 5 through 9)

The polysulfone oligomer obtained in Example 4 was impregnated on epoxysized T300/graphite fabric style (Union Carbide 35 million modulus fiber 24×24 weave) by first obtaining a 10 to 15% resin solids solution with methylene chloride. The solution was then coated onto the dry graphite fabric so that 38 percent by weight of the resulting prepreg would be the polysulfone oligomer. The prepreg was allowed to dry under ambient conditions to less than 1 percent volatile content. The prepreg was then cut into 6×6-inch pieces and stacked to obtain a consolidated composite of approximately 0.080 inch. The stack of prepreg was then vacuum bagged and consolidated under 100 psi in an autoclave heated to 625° F. for a minium period of 6 hours to cure. See the drawing.

Example 11

Resin used in this example was made in Example 4.

Prepreg Preparation

A graphite fabric prepreg, at 36 percent resin solids, was prepared by solvent impregnation from dilute methylene chloride solution. The graphite fabric was spread flat on a release film fluorinated ethylene-propylene copolymer made by duPont (FEP) in a fume hood. The approximately 10–15 percent prepregging solution was evenly swept into the fabric and allowed to air dry. This procedure was repeated, on alternating sides of the fabric, until the desired weight of resin had been applied. The prepreg was then dried 2 hours at 275° F. in an air-circulating oven.

Cure

Seven plies of the prepreg were stacked, double-wrapped in release-coated 2-mil Kapton film, and sealed in a vacuum bag for high-temperature cure as shown in the drawing. The thus-prepared stack was placed in an autoclave at 100 psi and, after raising the temperature 10° F. per minute to a temperature of 625° F., was heated for 6 hours.

Evaluation of Cured Composite

A short series of tests was conducted on the cured composite. The tests included solubility in methylene chloride, mechanical properties, and cursory reforming. To ensure that something unique had occurred with the resin of this example, a control panel was fabricated and underwent identical testing. The control panel consisted of the same graphite fabric impregnated with Union Carbide P1700 polysulfone. The only difference in the processing cycle was that 200 psi was required to consolidate the graphite/P1700 composite, whereas only vacuum pressure was required using the resin composite of the present invention. This is because the polysulfone has an initial molecular weight higher than the oligomer of the present invention. The molecular weight of the oligomer of the present invention increases during the curing reaction after consolidation of the composite at low pressure.

Solubility in Methylene Chloride

Samples of the two composites were machined into 1×0.5-inch coupons and placed in a bottle containing methylene chloride. The samples were observed until ply separation occurred. The results of the testing revealed conclusively that the P1700 graphite composite had ply separation in 3 hours, whereas the graphite composite of the present invention remained intact, with only slight swelling after immersion times to 2 months. This test amply demonstrated that the nadic imide cap had changed the character of the polysulfone system.

Mechanical Properties

The composites under consideration were machined into short beam shear specimens and tested at ambient conditions and 300° F. using the following procedure. The testing was accomplished on a flexure testing fixture using three-point loading with the span being equal to four times the specimen thickness. Results of testing are reported below:

|  | Short Beam Shear, ksi | |
| --- | --- | --- |
|  | Room Temperature | 300° F. |
| P1700 Composite | 7.07 | 5.14 |
| Nadic Imide Cap Composite | 7.61 | 5.41 |

Reforming Evaluation

To determine if the composite of the present invention could be reprocessed similarly to the P1700 polysulfone, a test was conducted in which a small coupon was reformed over a 90-degree angle. The flat coupon was placed on an aluminum angle and vacuum bagged. The assembly was placed in an autoclave and formed using the conventional P1700 cure schedule (i.e., 200 psi at 600° F. for 30 minutes). After removing the assembly from the vacuum bag, the previously flat specimen had reformed to the shape of the aluminum tool. The specimen was then mounted and photomicrographs were taken. It was determined that there was little or no deformation of the graphite fiber plies during the reforming operation. The end of the specimen indicated that the individual plies had moved sufficiently to permit the flat coupon to readily form over the 90-degree angle.

Example 12

Polysulfone oligomers were made using procedures described in Examples 7 and 8. Composite panels were fabricated as described in Example 10 and mechanical properties determined. See Table VII.

TABLE VII

Summary Intralaminar Shear Properties, Maleic-Capped Polysulfone Thermoplastics

| Panel Number[2] | Resin Used/Curative | Shear Strength, psi[1] at | |
| --- | --- | --- | --- |
|  |  | RT | 350° F. |
| 1 | (Example 7)/MDA[3] | 6210 | 4820 |
| 2 | (Example 8)/MDA[3] | 5170 | 2500 |
| 3 | (Example 8)/MDA[3] | 5310 | 4700 |

Cure Conditions:
RT to 450° F. at 5–6° F./minute, apply 100 psi, hold 2 hours
Postcure:
Panel No. 1: 12 hours at 600° F.
Panel No. 2: 6 hours at 625° F.
Panel No. 3: 6 hours at 625° F.

[1]Short beam shear test method
[2]Seven plies, 13-mil-thick T300 fabric, epoxy sized.
[3]MDA is 4,4' methylene dianiline.

Example 13

Prepreg Preparation and Laminate Consolidation—nadic imide cap resins

Two seven-ply laminates were prepared, one using a mixture of 80% by weight of the resin of Example 4 and 20% by weight of the resin of Example 9, and the other using the resin of Example 6. The physical and mechanical properties of each laminate were determined (Table VIII).

In each case, a weighed length of 13-mil T300 graphite fabric was laid flat on a release film of FEP. A dilute (approximately 10%) solution of the resin in methylene chloride was swept into the fabric, taking care to wet the fibers as well as possible. The prepreg was allowed to air dry and turned, and the procedures were repeated for the reverse side. Each laminate was placed in a vacuum bag and cured 7 hours under vacuum pressure plus 200 psi.

TABLE VIII

Physical and Mechanical Properties

|  | Resin Used in Composite | |
| --- | --- | --- |
|  | Example 6 | 80% Example 4 20% Example 9 |
| Laminate Physical Properties |  |  |
| Specific Gravity | 1.460 | 1.446 |
| Resin Content, percent | 37.1 | 34.1 |
| Percent Voids | 3.0 | 6.1 |
| Fiber Volume, percent | 53.2 | 54.4 |
| Laminate Mechanical Properties[1,2,3] |  |  |
| Interlaminar Shear Ultimate, ksi |  |  |
| RT | 7.01 | 7.23 |
| 300° F. | 4.18 | 4.68 |
| Flexure Strength, ksi (RT) | 77.3 | 83.3 |

TABLE VIII-continued

| | Physical and Mechanical Properties | |
|---|---|---|
| | Resin Used in Composite | |
| | Example 6 | 80% Example 4 20% Example 9 |
| Flexure Modulus, Msi (RT) | 8.1 | 10.2 |

[1] Panel cure: vacuum pressure RT to 625° F.; apply 200 psi, hold 7 hrs., cool.
[2] Seven-ply, 0.013-inch, T300 fabric, style 24 × 24.
[3] Both panels were insoluble in CH$_2$Cl$_2$ after cure.

It will be apparent to those skilled in the art that various modifications and variations could be made in the invention without departing from the scope or spirit of the invention.

What is claimed is:

1. A compound having the formula:

wherein X is selected from the group consisting of and R″ is lower alkyl.

2. A compound according to claim 1, wherein X is

3. A compound according to claim 1, wherein X is

4. A compound according to claim 1, wherein X is

* * * * *